(12) United States Patent
Aruga et al.

(10) Patent No.: US 12,169,287 B2
(45) Date of Patent: Dec. 17, 2024

(54) LIGHT EMITTING MODULE INCLUDING OPTICAL MEMBER THAT CONTROLS LIGHT DISTRIBUTION

(71) Applicant: NICHIA CORPORATION, Anan (JP)

(72) Inventors: Takanori Aruga, Suwa-gun (JP); Masahiro Imai, Chino (JP)

(73) Assignee: NICHIA CORPORATION, Anan (JP)

( * ) Notice: Subject to any disclaimer, the term of this patent is extended or adjusted under 35 U.S.C. 154(b) by 389 days.

(21) Appl. No.: 17/592,212

(22) Filed: Feb. 3, 2022

(65) Prior Publication Data

US 2022/0260758 A1 Aug. 18, 2022

(30) Foreign Application Priority Data

Feb. 17, 2021 (JP) ................. 2021-022963

(51) Int. Cl.
*G02B 3/00* (2006.01)
*A61L 2/26* (2006.01)
*F24F 13/22* (2006.01)
*G02B 27/09* (2006.01)
*H01L 33/58* (2010.01)
*H01L 33/48* (2010.01)

(52) U.S. Cl.
CPC ................. *G02B 3/00* (2013.01); *A61L 2/26* (2013.01); *F24F 13/22* (2013.01); *G02B 27/0955* (2013.01); *H01L 33/58* (2013.01); *A61L 2202/11* (2013.01); *F24F 2013/228* (2013.01); *G02B 2003/0093* (2013.01); *H01L 33/483* (2013.01)

(58) Field of Classification Search
CPC .................. G02B 3/00; G02B 27/0955; G02B 2003/0093; G02B 19/0014; G02B 19/0061; A61L 2/26; A61L 2202/11; H01L 33/58; H01L 33/483; H01L 33/54; F24F 2013/228
USPC .................................................... 250/453.11
See application file for complete search history.

(56) References Cited

U.S. PATENT DOCUMENTS

| | | |
|---|---|---|
| 2010/0118531 A1 | 5/2010 | Montagne |
| 2012/0014115 A1 | 1/2012 | Park et al. |
| 2012/0274203 A1 | 11/2012 | Yokotani |
| 2013/0161672 A1 | 6/2013 | Hsieh |

(Continued)

FOREIGN PATENT DOCUMENTS

| | | |
|---|---|---|
| CN | 101986018 A | 3/2011 |
| CN | 102221178 A | 10/2011 |

(Continued)

*Primary Examiner* — Jason L McCormack
(74) *Attorney, Agent, or Firm* — Foley & Lardner LLP (57) ABSTRACT

A light emitting module includes: a light source; and an optical member configured to control a distribution of light emitted from the light source. The optical member comprises an incident face on which the light from the light source is incident, and an output face through which the light incident on the incident face exits. In a plan view: the optical member is shaped to have a long axis and a short axis orthogonal to the long axis, and a central axis of the optical member passes through a center of the light source, a center of the incident face, and a center of the output face, while being orthogonal to a long axis direction parallel to the long axis and a short axis direction parallel to the short axis.

18 Claims, 5 Drawing Sheets (56) References Cited

U.S. PATENT DOCUMENTS

| | | | |
|---|---|---|---|
| 2013/0229810 A1* | 9/2013 | Pelka | G02B 19/0061 |
| | | | 362/311.06 |
| 2014/0117394 A1* | 5/2014 | Kim | F21V 5/04 |
| | | | 257/98 |
| 2015/0192255 A1* | 7/2015 | Kim | G02B 5/021 |
| | | | 362/335 |
| 2015/0276170 A1 | 10/2015 | Motoyanagi et al. | |
| 2015/0308653 A1 | 10/2015 | Wang et al. | |
| 2016/0201875 A1* | 7/2016 | Kang | G02B 19/0014 |
| | | | 362/311.06 |
| 2016/0290573 A1* | 10/2016 | Allen | H05B 45/20 |
| 2017/0234507 A1 | 8/2017 | Kang | |
| 2019/0323665 A1 | 10/2019 | Okahisa | |

FOREIGN PATENT DOCUMENTS

| | | |
|---|---|---|
| CN | 202442262 U | 9/2012 |
| JP | 2010-524170 A | 7/2010 |
| JP | 2010-177028 A | 8/2010 |
| JP | 2011-040315 A | 2/2011 |
| JP | 2012-129153 A | 7/2012 |
| JP | 2012-231036 A | 11/2012 |
| JP | 2013-516785 A | 5/2013 |
| JP | 2013-138207 A | 7/2013 |
| JP | 2014-146530 A | 8/2014 |
| JP | 2015-507350 A | 3/2015 |
| JP | 2015-195377 A | 11/2015 |
| JP | 2017-147227 A | 8/2017 |
| JP | 2019-192386 A | 10/2019 |
| JP | 2019-207818 A | 12/2019 |
| WO | WO-2011/104404 A1 | 9/2011 |

\* cited by examiner

LIGHT EMITTING MODULE INCLUDING OPTICAL MEMBER THAT CONTROLS LIGHT DISTRIBUTION

CROSS-REFERENCE TO RELATED APPLICATION

This application claims priority to Japanese Patent Application No. 2021-022963, filed on Feb. 17, 2021, the disclosure of which is hereby incorporated by reference in its entirety.

BACKGROUND

The present disclosure relates to a light emitting module.

Japanese Patent Publication No. 2010-524170 discloses a light emitting module which includes a light emitting diode chip and a lens that disperses the luminous flux of the light released from the light emitting diode chip.

It is desirable for a light emitting module to have the characteristic of broadening the light distribution in a long axis direction of an optical member such as a lens, to thereby have a broader light distribution in the long axis direction. One of the objects of the present disclosure is to provide a light emitting module capable of broadening the light distribution in the long axis direction of the optical member, to thereby achieve a broader light distribution in the long axis direction.

According to one embodiment of the present disclosure, a light emitting module includes a light source; and an optical member configured to control a distribution of light emitted from the light source. The optical member comprises an incident face on which the light from the light source is incident, and an output face through which the light incident on the incident face exits. In a plan view: the optical member is shaped to have a long axis and a short axis orthogonal to the long axis, and a central axis of the optical member passes through a center of the light source, a center of the incident face, and a center of the output face, while being orthogonal to a long axis direction parallel to the long axis and a short axis direction parallel to the short axis. In a long axis cross section of the optical member, in a plane that includes the long axis and the central axis: the incident face is concave shaped and has a curved face portion that intersects the central axis, and the output face has a concave portion positioned in a region that includes the central axis, and convex portions that are at both ends of and are continuous with the concave portion. In a short axis cross section of the optical member, in a plane that includes the short axis and the central axis: the incident face is concave shaped and has a flat face portion that intersects the central axis and is parallel to the short axis direction, and the output face is convex shaped. In a plan view, the light source is disposed in a region in which the incident face is positioned. In the long axis cross section, a minimum distance between the light source and the incident face is smaller than a minimum distance between the light source and the incident face in the short axis cross section.

A light emitting module according to certain embodiments of the present disclosure is capable of broadening the light distribution in the long axis direction of the optical member and achieving a broader light distribution in the long axis direction can be provided.

DETAILED DESCRIPTION

Certain embodiments of a light emitting module according to the present invention will be explained below. The drawings referred in the description below are schematic representation of the present invention, and as such, the relative sizes of, positional relationship, and spacing between the members might be exaggerated, or certain members might be omitted. Moreover, the relative sizes of and spacing between the members might not match between a top view and a cross-sectional view. In the description below, the same designations and reference numerals denote the same or similar members as a rule, for which detailed explanation might be omitted as appropriate.

Figure 1:
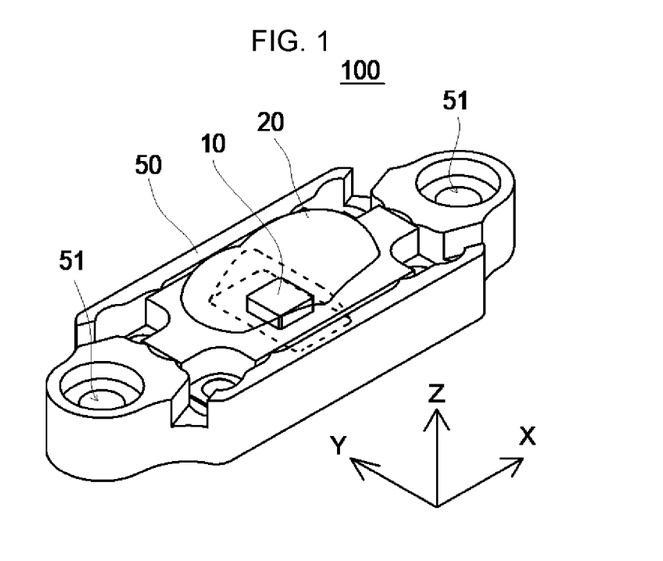
FIG. 1 is a schematic perspective view of a light emitting module according to one embodiment of the present invention.

FIG. 1 is a schematic perspective view of a light emitting module 100 according to one embodiment of the present invention. The light emitting module 100 has a light source 10 and an optical member 20 that controls the distribution of the light emitted from the light source 10. The casing 50 has a recessed part, and the light source 10 and the optical member 20 are arranged in the recessed part of the casing 50.

For the light source 10, a light emitting element such as a light emitting diode, a light emitting device that is a light emitting element mounted in a package, or the like can be used. For the package material used for such a light emitting device, a ceramic or resin can be used. The peak emission wavelength of the light from the light source 10 is, for example, 250 nm to 600 nm. For example, by using a light source 10 which emits UV light, the light emitting module 100 can be used for sterilization or sanitization purposes. The peak emission wavelength for a UV light emitting light source 10, for example, is 310 nm at most. In a plan view, the shape of the light source 10 is, for example, substantially quadrangular. In the present embodiment, the light source 10 is substantially square shaped in a plan view. In a plan view, the light source 10 can be a square, each side being in a range of 0.5 mm to 4 mm, for example. The center of the light source 10 is positioned in the center of the shape of the light source 10 in a plan view.

Figure 2:
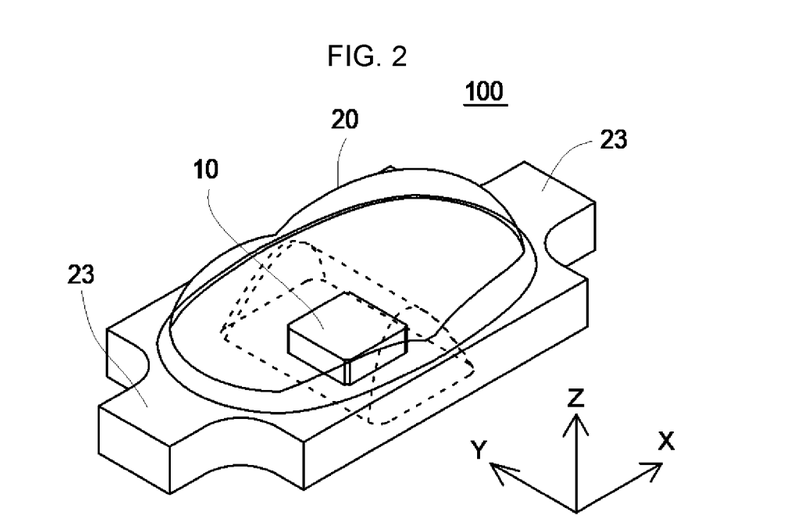
FIG. 2 is a schematic perspective view explaining the arrangement of the light source and the optical member of the light emitting module according to the embodiment of the present invention.
Figure 3A:
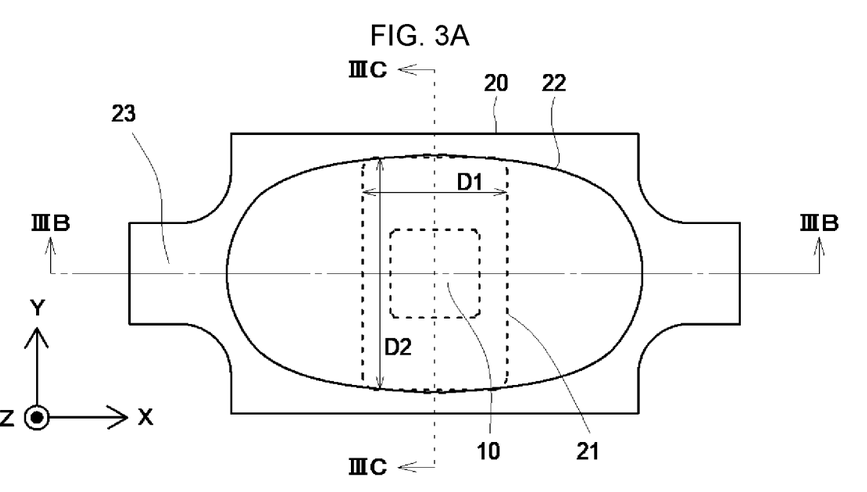
FIG. 3A is a schematic top view of the light emitting module according to the embodiment of the present invention.
Figure 3B:
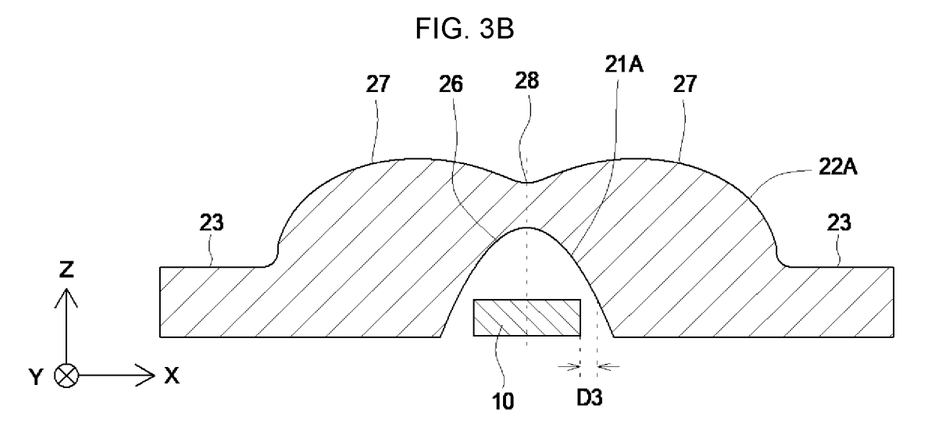
FIG. 3B is a schematic cross-sectional view taken along line IIIB-IIIB in FIG. 3A.
Figure 3C:
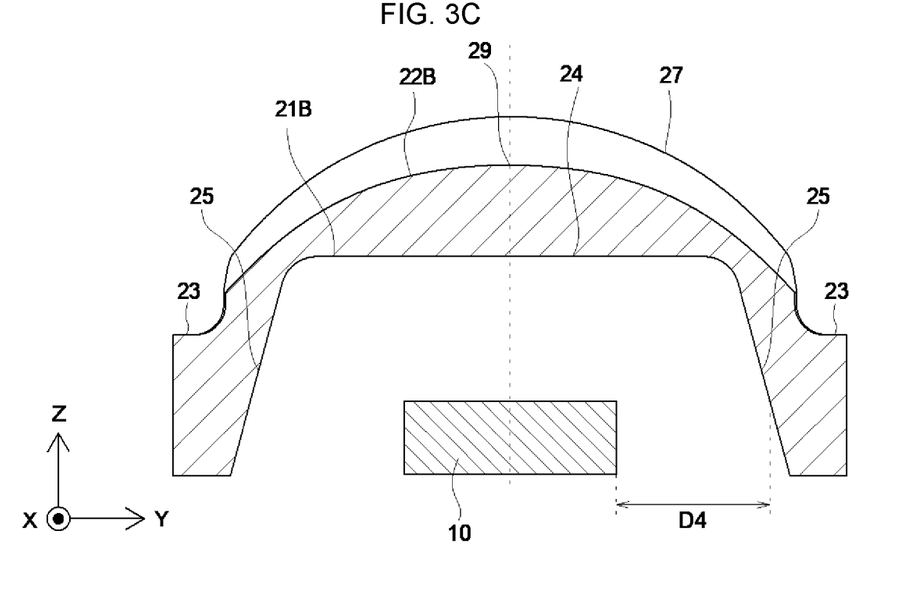
FIG. 3C is a schematic cross-sectional view taken along line IIIC-IIIC in FIG. 3A.

FIG. 2 is a schematic perspective view explaining the arrangement of the light source 10 and the optical member 20 of the embodiment of the present invention. FIG. 3A is a schematic top view of the light emitting module 100 according to the embodiment of the present invention. FIG. 3B is a schematic cross-sectional view taken along line IIIB-IIIB in FIG. 3A. FIG. 3B is a long axis cross section of the optical member 20 in the plane that includes the long axis and the central axis of the optical member 20. FIG. 3C is a schematic cross-sectional view taken along line IIIC-IIIC in FIG. 3A. FIG. 3C is a short axis cross section of the optical member 20 in the plane that includes the short axis and the central axis of the optical member 20.

As shown in FIG. 2, the optical member 20 is disposed to cover the light source 10. As shown in FIG. 3A, the optical member 20 is shaped to have a long axis, and a short axis orthogonal to the log axis in the plan view. The central axis of the optical member 20 passes through a center of the light source 10, a center of the incident face 21, and a center of the output face 22, while being orthogonal to the long and short axes. The direction parallel to a long axis of the optical member 20 is defined as the long axis direction X. The direction parallel to a short axis of the optical member 20 is defined as the short axis direction Y. The direction orthogonal to the long axis direction X and the short axis direction Y is defined as the central axis direction Z. The central axis of the optical member 20 extends along the direction that is parallel to the central axis direction Z.

The optical member 20 is shaped to have a length in the long axis direction X that is larger than a length in the short axis direction Y. The length L1 of the optical member 20 in the long axis direction X can be set in a range of 150% to 200% of the length L2 of the optical member 20 in the short axis direction Y. Setting the length L1 of the optical member 20 to at least 150% of the length L2 of the optical member 20 allows the convex portions 27 described later to be broader, thereby facilitating the achievement of a broader light distribution in the long axis direction X. Setting the length L1 of the optical member in a range of 20 to 200% of the length L2 of the optical member 20 at most allows the flat face portion 24 described later to have a larger area while maintaining the strength of the optical member 20. The length of the optical member 20 in the long axis direction X can be set in a range of 15 mm to 20 mm, for example. The length of the optical member 20 in the short axis direction Y can be set in a range of 5 mm to 10 mm, for example. Here, the length of the optical member 20 in the long axis direction X is the maximum length of the output face 22 described later along the long axis direction X in a plan view. The length of the optical member 20 in the short axis direction Y described above is the maximum length of the output face 22 described later along the short axis direction Y in a plan view.

As shown in FIG. 2 and FIG. 3A, the optical member 20 has a peripheral part 23 which surrounds the region in which the output face 22 is located. The peripheral part 23 is the portion through which the light exiting the light source 10 barely transmits, hardly affecting the light distribution control over the light from the light source 10. The peripheral part 23 has a larger length in the long axis direction X than the length in the short axis direction Y. Indentations are provided in the adjacent positions at both ends of the peripheral part 23 in the long axis direction X indenting from the outline of the optical member 20 towards the output face 22. The surface of the peripheral part 23 does not include the incident face 21 or the output face 22.

As shown in FIG. 3A to FIG. 3C, the optical member 20 includes an incident face 21 on which the light from the light source 10 is incident, and an output face 22 through which the light from the light source 10 exits. The light from the light source 10 passes through the incident face 21 and the output face 22 to be extracted out.

As shown in FIG. 3A, in a plan view, the length D1 along the long axis direction X of the region in which the incident face 21 is provided is smaller than the length D2 along the short axis direction Y of the region in which the incident face 21 is provided. The length D1 along the long axis direction X of the region in which the incident face 21 is provided can be set in a range of 50% to 70% of the length D2 along the short axis direction Y of the region in which the incident face 21 is provided. This can increase the area of the flat face portion 24 of the second incident face 21B described later to allow the light to be readily refracted towards the central axis of the light source 10 while allowing the first incident face 21A described later to efficiently collect the light from the light source 10. The length D1 along the long axis direction X of the region in which the incident face 21 is provided can be set in a range of 3 mm to 7 mm, for example. The length D2 along the short axis direction Y of the region in which the incident face 21 is provided can be set in a range of 7 mm to 15 mm, for example. The length of the region in which the incident face 21 is provided along the long axis direction X or the short axis direction Y is the maximum length among the lengths along the long axis direction X or the short axis direction Y. In a plan view, the region in which the incident face 21 is provided has a rectangular shape with long sides along the short axis direction Y. In a plan view, the light source 10 is disposed in the region in which the incident face 21 is positioned. In a plan view, the size of the light source 10 is smaller than the size of the region in which the incident face 21 is positioned.

As shown in FIG. 3B, the incident face 21 of the optical member 20 in the long axis cross section is concave shaped. Hereinafter, the incident face 21 of the optical member 20 in the long axis cross section might occasionally be referred to as the first incident face 21A. The first incident face 21A has a curved face portion 26 that intersects the central axis of the light source 10. Positioning the curved face portion 26 directly above the light source 10 can restrain the light near the central axis of the light source 10 from being output narrowly in the long axis direction X. From the perspective of allowing the light from the light source 10 to be output broadly in the long axis direction X, an entirety of the first incident face 21A is preferably curved.

As shown in FIG. 3B, the output face 22 of the optical member 20 in the long axis cross section has a concave portion 28 in the region that includes the central axis of the light source 10, and convex portions 27 continuous with the concave portion 28 positioned at both ends of the concave portion 28. The output face 22 of the optical member 20 in the long axis cross section might hereinafter occasionally be referred to as the first output face 22A. The first output face 22A in the long axis cross section is one continuous curved face made up of the convex portions 27 and the concave portion 28. The concave portion 28 positioned directly above the light source 10 can refract the light near the central axis of the light source 10 in the directions to broaden the light distribution in the long axis direction X. Furthermore, the convex portions 27 positioned at both ends of the concave portion 28 can spread the light from the light source 10 in the long axis direction X. In other words, shaping the first output face 22A as described above can spread the light from the light source 10 that is incident on the first output face 22A in the long axis direction X thereby achieving for the light emitting module 100 a batwing light distribution that is broad in the long axis direction X.

In the central axis direction Z, the height of the concave portion 28 is lower than the heights of the convex portions 27. The height difference between the concave portion 28 and the convex portions 27 can be set, for example, in a range of 0.7 mm to 1 mm. The maximum height of the convex portions 27 can be set, for example, in a range of 5 mm to 7 mm. The height of the concave portion 28 can be set, for example, in a range of 4 mm to 6 mm.

As shown in FIG. 3C, the incident face 21 of the optical member 20 in the short axis cross section is concave shaped. The incident face 21 of the optical member 20 in the short axis cross section might occasionally be referred to as the second incident face 21B below. The second incident face 21B has a flat face portion 24 which intersects the central axis of the light source 10 and is parallel to the short axis direction Y. Providing a flat face portion 24 in the second incident face 21B allows the light from the light source 10 that is incident on the flat face portion 24 to refract towards the central axis of the light source 10, thereby narrowing the light distribution in the short axis direction Y. The length of the flat face portion 24 is preferably set to two to three times the length of the light source 10 in the short axis direction Y. Setting the length of the flat face portion 24 as two to three times the length of the light source 10 in the short axis direction Y allows the light from the light source 10 to readily become incident on the flat face portion 24, thereby making the light distribution in the short axis direction Y narrower. The length of the flat face portion 24 can be set, for example, in a range of 5 mm to 10 mm. The flat face portion 24 is positioned higher than the upper face of the peripheral part 23.

The second incident face 21B has a linear lateral face portion 25 that is continuous with the flat face portion 24 and oblique to the central axis in the short axis cross section. The lateral face portion 25 forms an oblique angle of 60 to 95 degrees with the central axis, for example. The flat face portion 24 and the lateral face portion 25 are connected via a curved face.

The output face 22 of the optical member 20 in the short axis cross section is convex shaped. The output face 22 of the optical member 20 in the short axis cross section might occasionally be referred to as the second output face 22B below. The second output face 22B has a curved face portion 29 that intersects the central axis of the light source 10. Providing a curved face portion 29 directly above the light source 10 allows the curved face portion to collect the light that passed through the second incident face 21B, thereby restraining the outgoing light from spreading in the short axis direction Y. From the perspective of allowing the light from the light source 10 to be output narrowly in the short axis direction Y, the second output face 22B is preferably a curved face in its entirety.

As shown in FIG. 3B and FIG. 3C, the minimum distance D3 between the light source 10 and the incident face 21 along the long axis direction X is smaller than the minimum distance D4 between the light source 10 and the incident face 21 along the short axis direction Y. This allows the light from the light source 10 to readily become incident on the first incident face 21A in the long axis direction X, while securing the area for the flat face portion 24 in the short axis direction Y. In the long axis cross section, the minimum distance D3 between the light source 10 and the incident face 21 along the long axis direction X is, for example, in a range of 0.3 mm to 1 mm. In the short axis cross section, the minimum distance D4 between the light source 10 and the incident face 21 along the short axis direction Y is, for example, in a range of 2 mm to 4 mm.

In the central axis direction Z, the distance between the light source 10 and the incident face 21 can be set, for example, in a range of 1.5 mm to 3 mm.

For the optical member 20, a material having light transmissivity with respect to the light from the light source 10 is used. For the material for the optical member 20, for example, a resin such as acrylic, cycloolefin, cycloolefin copolymer, epoxy, silicone, or the like can be used.

Figure 4:
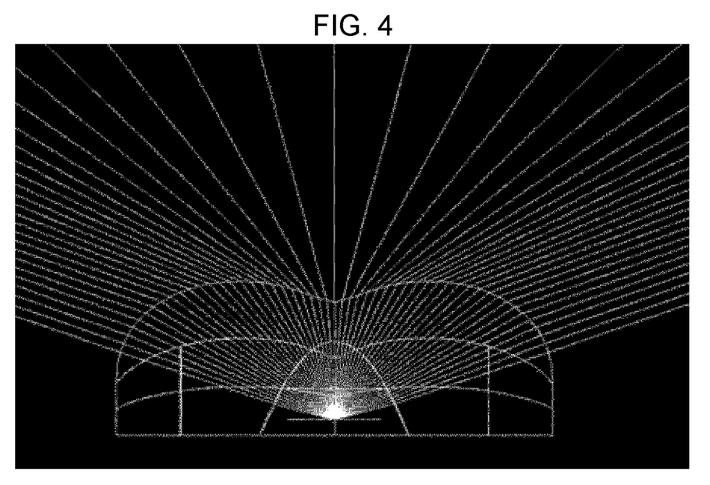
FIG. 4 is a schematic diagram showing the optical paths of the embodiment of the present invention.
Figure 5:
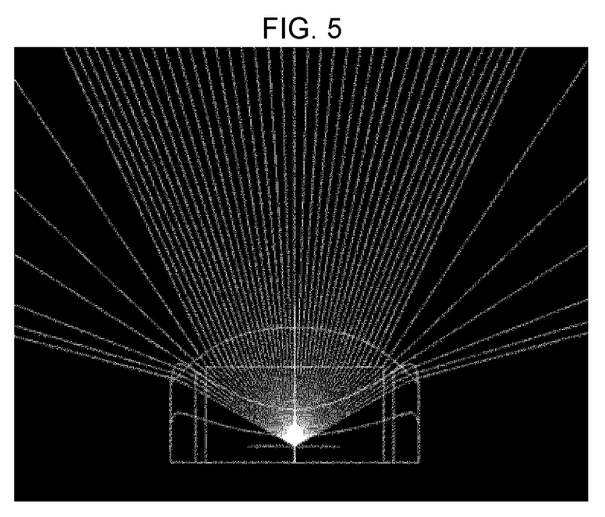
FIG. 5 is a schematic diagram showing the optical paths of the embodiment of the present invention.

FIG. 4 and FIG. 5 are schematic diagrams showing the optical paths of the light rays exiting the center of a light source 10 and entering an optical member 20 when the optical member 20 according to the present embodiment is employed. FIG. 4 shows the optical paths in the long axis cross section, and FIG. 5 shows the optical paths in the short axis cross section. It can be understood from FIG. 4 that extracting the light emitted by the light source 10 through the first incident face 21A and the first output face 22A broadens the light distribution. It can be understood from FIG. 5 that extracting the light emitted by the light source 10 through the second incident face 21B and the second output face 22B narrows the light distribution. For example, the rays of light passing through the flat face portion 24 of the second incident face 21B are refracted towards the central axis of the light source 10 to thereby narrow the light distribution.

Figure 6:
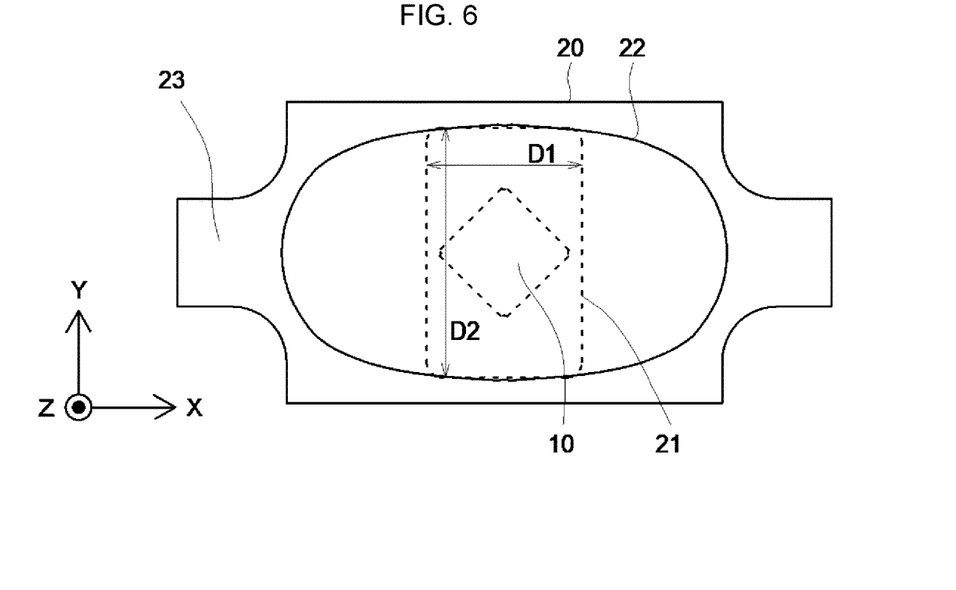
FIG. 6 is a schematic top view of a light emitting module variation of the present invention.

FIG. 6 is a schematic top view of a variation of the present embodiment. The variation shown in FIG. 6 has substantially the same construction as that of the light emitting module 100 except for the orientation of the light source 10.

In the light emitting module 100 shown in FIG. 3A, the light source 10 is placed such that each side is parallel to the long axis direction X or the short axis direction Y, whereas in the variation of the embodiment shown in FIG. 6, the light source 10 is placed such that each side forms about a 45-degree angle with the long axis direction X or the short axis direction Y. Placing a light source 10 in this manner to allow each side of the emission face to form about a 45 degree angle with the long axis direction X or the short axis direction Y can reduce the distance from the center of the light source 10 to a side of the light source 10 in the direction that is about 45 degrees oblique to the long axis direction X or the short axis direction Y as compared to that in the case of the light emitting module 100 shown in FIG. 3A. This makes it easier to achieve the optical design required for a light distribution that is broad in the long axis direction X than in the case in which the light source 10 is arranged such that each side of the light source 10 is parallel to the long axis direction X or the short axis direction Y. In the case of using a light emitting device as the light source 10, the package which mounts a light emitting element may be placed such that each side of the package is parallel to the long axis direction X or the short axis direction Y while orienting the light emitting element such that each side of the emission face is about 45 degrees oblique to the long axis direction X or the short axis direction Y.

Figure 7:
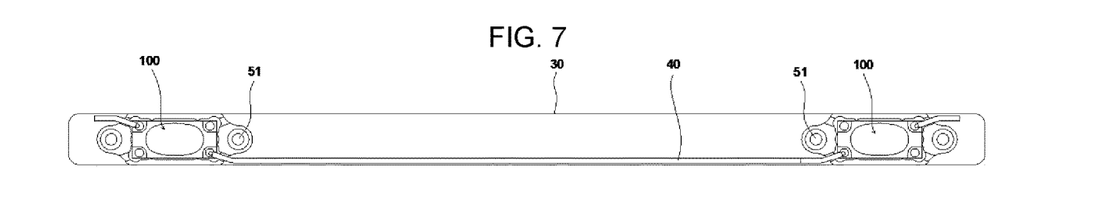
FIG. 7 is a schematic top view explaining an application example in which a light emitting module according to the embodiment of the present invention is employed.
Figure 8:
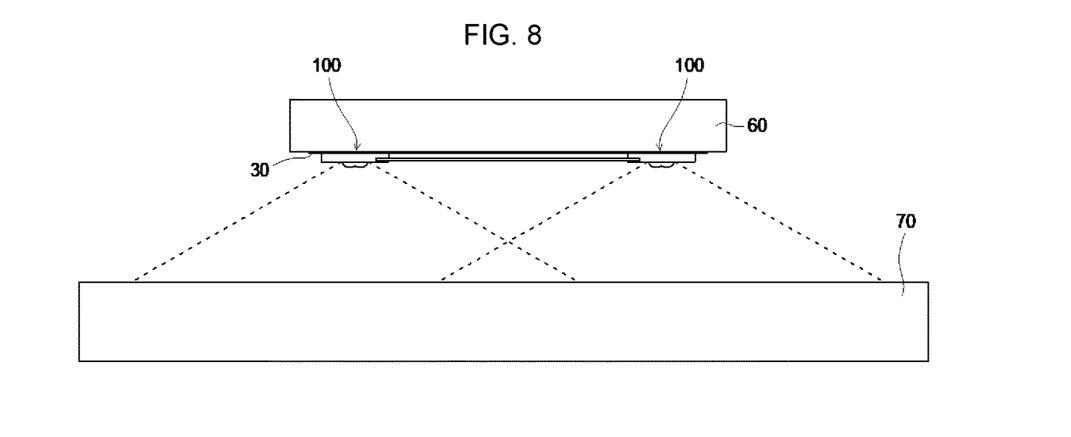
FIG. 8 is a schematic side view explaining the application example in which a light emitting module according to the embodiment of the present invention is employed.

FIG. 7 and FIG. 8 are schematic diagrams showing an application example of a light emitting module 100 according to the embodiment. In this application example, two light emitting modules 100 are arranged on a support substrate 30, and the two light emitting modules 100 are electrically connected via a conductive member 40. The shape of the support substrate 30 in a plan view can be, for example, rectangular. In a top view, the straight line connecting the centers of the light sources 10 of the two light emitting modules 100 preferably is parallel to the long sides of the support substrate 30. The distance between the two light emitting modules 100 can be set, for example, in a range of 150 mm to 250 mm. Here, the distance between the two light emitting modules is the distance between the centers of the light sources 10 of the light emitting modules 100. Arranging the light emitting modules 100 on a rectangular support substrate 30 can achieve a light distribution that is broad in the longitudinal direction of the support substrate 30. In the case of irradiating light on a long narrow area by using a light emitting module 100, for example, using this application example can efficiently irradiate light on the rectangular area. As shown in FIG. 8, the support substrate 30 which is bonded to a support 60 is positioned so as to oppose the light emitting modules 100 to the surface of a base body 70 to be irradiated. Such an arrangement allows the light from the light emitting modules 100 to broaden in the longitudinal direction of the support substrate 30 as indicated by the dotted lines in FIG. 8 to irradiate the surface of the base body 70 along the longitudinal direction of the support substrate 30.

For the casing 50, for example, a resin, such as polycarbonate, epoxy, and silicone, or a fluorine-based resin can be used. As shown in FIG. 1 and FIG. 7, each casing 50 has circular holes 51 outward from the optical member 20 in the long axis direction X, and each light emitting module 100 can be secured to the base substrate 30 using screws or the like inserted into the holes 51. In the recessed part of each casing 50, a base made of aluminum, or the like is bonded via a bonding member. For the base, a glass epoxy substrate or glass composite substrate may alternatively be used. Each light source 10 is disposed on a base, and electrically connected to the base. Portions of each base are exposed in the regions corresponding to the indentations of the peripheral part 23, and the conductive member 40 is electrically connected to the exposed portions of the base. After electrically connecting each base to the conductive member 40, a resin or the like can be used to coat the connected parts to achieve a water-proof structure.

A light emitting module 100 according to the present invention can be used, for example, to irradiate light on the drain pan and the heat exchanger in an air conditioner, for example, for the purpose of reducing mold growth in the drain pan. Furthermore, employing a light emitting module 100 according to the present invention in a humidifier, air purifier, or the like can also be considered effective in reducing mold growth.

What is claimed is:

1. A light emitting module comprising:
   a light source; and
   an optical member configured to control a distribution of light emitted from the light source; wherein:
   the optical member comprises an incident face on which the light from the light source is incident, and an output face through which the light incident on the incident face exits,
   in a plan view:
      the optical member is shaped to have a long axis and a short axis orthogonal to the long axis, and
      a central axis of the optical member passes through a center of the light source, a center of the incident face, and a center of the output face, while being orthogonal to a long axis direction parallel to the long axis and a short axis direction parallel to the short axis;
   in a long axis cross section of the optical member, in a plane that includes the long axis and the central axis:
      the incident face is concave shaped and has a curved face portion that intersects the central axis, and
      the output face has a concave portion positioned in a region that includes the central axis, and convex portions that are at both ends of and are continuous with the concave portion;
   in a short axis cross section of the optical member, in a plane that includes the short axis and the central axis:
      the incident face is concave shaped and has a flat face portion that intersects the central axis and is parallel to the short axis direction, and
      the output face is convex shaped;
   in a plan view, the light source is disposed in a region in which the incident face is positioned;
   in the long axis cross section, a minimum distance between the light source and the incident face is smaller than a minimum distance between the light source and the incident face in the short axis cross section; and
   a length of the flat face portion is in a range of two to three times a length of the light source in the short axis direction.

2. The light emitting module according to claim 1, wherein, in the short axis cross section, the incident face has a linear lateral face portion that is continuous with the flat face portion and oblique to the central axis.

3. The light emitting module according to claim 1, wherein, in the long axis cross section, an entirety of the incident face is curved.

4. The light emitting module according to claim 2, wherein, in the long axis cross section, an entirety of the incident face is curved.

5. The light emitting module according to claim 1, wherein:
   in the long axis cross section, the minimum distance between the light source and the incident face along the long axis direction is in a range of 0.3 mm to 1 mm, and
   in the short axis cross section, the minimum distance between the light source and the incident face along the short axis direction is in a range of 2 mm to 4 mm.

6. The light emitting module according to claim 2, wherein:
   in the long axis cross section, the minimum distance between the light source and the incident face along the long axis direction is in a range of 0.3 mm to 1 mm, and
   in the short axis cross section, the minimum distance between the light source and the incident face along the short axis direction is in a range of 2 mm to 4 mm.

7. The light emitting module according to claim 3, wherein:
   in the long axis cross section, the minimum distance between the light source and the incident face along the long axis direction is in a range of 0.3 mm to 1 mm, and
   in the short axis cross section, the minimum distance between the light source and the incident face along the short axis direction is in a range of 2 mm to 4 mm.

8. The light emitting module according to claim 1, wherein, in a plan view, a length of the region in which the incident face is provided along the long axis direction is smaller than a length of the region in which the incident face is provided along the short axis direction.

9. The light emitting module according to claim 2, wherein, in a plan view, a length of the region in which the incident face is provided along the long axis direction is smaller than a length of the region in which the incident face is provided along the short axis direction.

10. The light emitting module according to claim 3, wherein, in a plan view, a length of the region in which the incident face is provided along the long axis direction is smaller than a length of the region in which the incident face is provided along the short axis direction.

11. The light emitting module according to claim 8, wherein, in a plan view, the length of the region in which the incident face is provided along the long axis direction is in a range of 50% to 70% of the length of the region in which the incident face is provided along the short axis direction.

12. The light emitting module according to claim 9, wherein, in a plan view, the length of the region in which the incident face is provided along the long axis direction is in a range of 50% to 70% of the length of the region in which the incident face is provided along the short axis direction.

13. The light emitting module according to claim 10, wherein, in a plan view, the length of the region in which the incident face is provided along the long axis direction is in a range of 50% to 70% of the length of the region in which the incident face is provided along the short axis direction.

14. The light emitting module according to claim 1, wherein the light source is configured to emit UV light.

15. The light emitting module according to claim 2, wherein the light source is configured to emit UV light.

16. The light emitting module according to claim 1, wherein, in the long axis cross section, an entirety of the incident face has a shape of a continuous curve without any discontinuities.

17. The light emitting module according to claim 1, wherein the light source is located in a cavity of the optical member defined by the incident face.

18. The light emitting module according to claim 1, wherein the light source is the only light source included in the light emitting module.

* * * * *